United States Patent [19]

Dezza et al.

[11] Patent Number: 5,026,374
[45] Date of Patent: Jun. 25, 1991

[54] BOLT FOR ORTHOPAEDIC SURGICAL USE

[75] Inventors: Ottavio Dezza, Bergamo; Giovanni Faccioli, Donatori di Sangue Monzambano, both of Italy

[73] Assignee: Orthofix S.r.l., Bussolengo VR, Italy

[21] Appl. No.: 415,991

[22] Filed: Oct. 2, 1989

[30] Foreign Application Priority Data

May 12, 1989 [IT] Italy ............... 84929 A/89

[51] Int. Cl.⁵ ............... A61F 5/04; E01B 9/10
[52] U.S. Cl. ............... 606/72; 606/73; 411/378
[58] Field of Search ............... 128/92; 606/65, 72, 606/104, 73, 79, 80, 62; 411/411, 412, 413, 424, 386, 378

[56] References Cited

U.S. PATENT DOCUMENTS

| | | | |
|---|---|---|---|
| 31,749 | 10/1859 | North | 411/411 |
| 411,152 | 9/1889 | Kuhn | 411/411 |
| 440,331 | 11/1890 | Rogers | 411/424 |
| 461,621 | 10/1891 | Rogers | 411/424 |
| 470,804 | 3/1892 | Jones | 411/424 |
| 1,969,796 | 8/1934 | Hoke | 411/424 |
| 1,988,925 | 1/1935 | Thomson | 411/424 |
| 3,051,169 | 8/1962 | Grath | 606/65 |
| 3,118,444 | 1/1964 | Serrato, Jr. | 606/104 |
| 4,338,054 | 7/1982 | Dahl | 411/424 |
| 4,653,244 | 3/1987 | Farrell | 411/412 |

*Primary Examiner*—Mickey Yu
*Assistant Examiner*—Michael Brown
*Attorney, Agent, or Firm*—Ladas & Parry

[57] ABSTRACT

The invention relates to a bolt for orthopaedic surgical use which can be combined with an external fixing device such as for example a monoaxial extender, having a substantially cylindrical upper portion 10 whose upper end 14 can be engaged by a suitable turning device. The bolt extends into a central portion 11 whose lateral surface has a cutting member 16 which extends parallel to the longitudinal axis of the bolt along the entire length of portion 11. Portion 11 then passes into a lower threaded portion 12 which ends in a point 13. Central portion 11 has a transverse cross-section substantially in the shape of a drop.

11 Claims, 1 Drawing Sheet

BOLT FOR ORTHOPAEDIC SURGICAL USE

The present invention relates to a bolt for orthopaedic surgical use, which in particular may be used in combination with an external fixing device, such as a monoaxial extender.

Known bolts used in the elongation of limbs through the use of monoaxial extender devices generally have a cylindrical portion followed by a tapered portion terminating in a point having a varying degree of sharpness. In this case, the tapered portion is threaded and the thread may be a tapered spiral thread or a cylindrical spiral thread. There are, however, also bolts having a completely cylindrical section with a thread which is restricted to a portion close to the point, equal to about one third of the total length of the bolt. All the types of bolts described above have circular transverse cross-sections over almost the entire length of the bolt. Generally the only exception to this is the end opposite the point which has a short suitably shaped portion whose function is to permit the bolt to be turned by means of a suitable instrument. When a segment of bone is to be extended at least two bolts are applied to both sides of the point at which the bone which is to be extended is cut, and then the extender device is fitted to the heads of the bolts projecting from the patient's skin and extension then takes place.

Normally a bolt is of such dimensions that the threaded portion is almost completely inserted into the bone, and therefore the portion of the bolt which projects from the bone and which is in contact with the soft tissues and the patient's skin is a generally cylindrical or frustoconical portion having a smooth lateral surface. During the movements due to extension this portion of the bolt, which normally has a diameter of some 6 mm, compresses the soft tissues with which it is in contact. This compression often gives rise to the occurrence of cutaneous or subcutaneous necrosis close to the point stressed.

This disadvantage is most obvious in achondroplastic patients of the female sex who have a subcutaneous panniculus adiposus.

The excessive pressure applied can also give rise to retraction scars which are aesthetically and functionally unacceptable to the patient.

The object of the invention is to at least minimise the abovementioned disadvantages and in particular to provide a bolt which reduces compression of the surrounding soft tissues to a minimum while maintaining unaltered the required strength characteristics.

According to the present invention there is provided a bolt for orthopaedic surgical use, which can be combined with an external fixing device, said bolt comprising a substantially cylindrical upper portion having an upper end which can be used to tighten the bolt by means of a suitable instrument, and extending into a lower threaded portion which terminates at its end in a point in which a central portion is provided between said upper and lower portions, the lateral surface of said central portion having a cutting member which extends parallel to the longitudinal axis of the bolt over the entire length of the central portion, and in which the ends of the lateral surface of the said portion are graded into the lateral surfaces of the said portion are graded into the lateral surfaces of the upper portion and the lower portion.

The main advantage offered by the arrangement proposed lies in the fact that a bolt according to the invention avoids occurrence of the cutaneous or subcutaneous necrosis mentioned, thus reducing suffering by the patient.

Another advantage is due to the fact that full thickness incisions under local anaesthetic, which make it necessary for the patient to be admitted to hospital, are no longer necessary.

A further advantage is due to the fact that medical checks during the entire elongation process can be reduced appreciably, and can take place at less frequent intervals.

As a result of this the patient, who is normally in his own home, has to make less journeys from home to hospital and doctors who are less involved in such checks can thus dedicate their time to other patients.

The present invention will be further illustrated, by way of example, with reference to the accompanying drawings, in which.

In the drawings, identical or equivalent parts have the same reference numerals.

Figure 1:
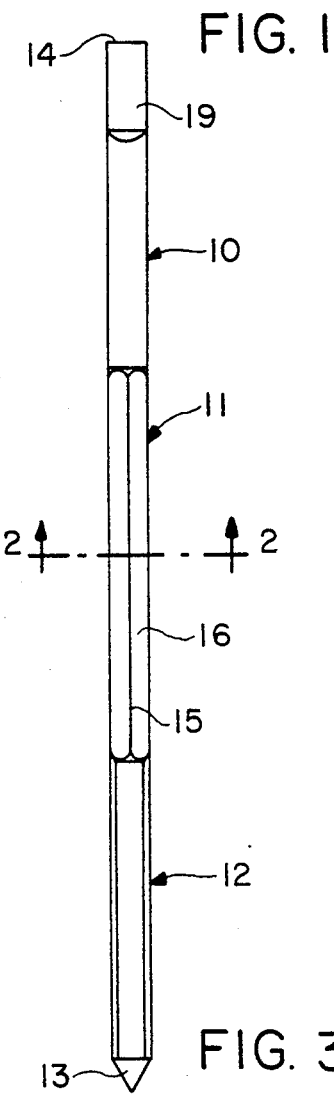
FIG. 1 is a side view of a bolt according to the invention.

As illustrated in FIG. 1, a bolt, of a substantially cylindrical shape, is constructed having an initial portion 10, a central portion 11 and a terminal portion 12.

Initial portion 10, which is perfectly cylindrical and of a length equal to about one third of the entire length of the bolt, has a short portion at upper end 14 in which the lateral surface is flattened in order to allow a suitable instrument to tighten up or slacken off the said bolt.

Terminal portion 12 is cylindrical, having an external diameter equal to the diameter of portion 10, is threaded externally and ends at its lower end in a tapering point 13.

Central portion 11 constitutes the fundamental characteristic of the invention.

The lateral surface of said central portion 11 has a cutting member 16 which extends parallel to the longitudinal axis of the bolt along the entire length of portion 11. The ends of the lateral surface of said portion 11 merge into the lateral surfaces of preceding portion 10 and following portion 12 so as to avoid forming sharp edges which could harm anyone handling the bolt too casually, in addition to causing problems when the bolt is positioned in the patient's bone.

Figure 2:
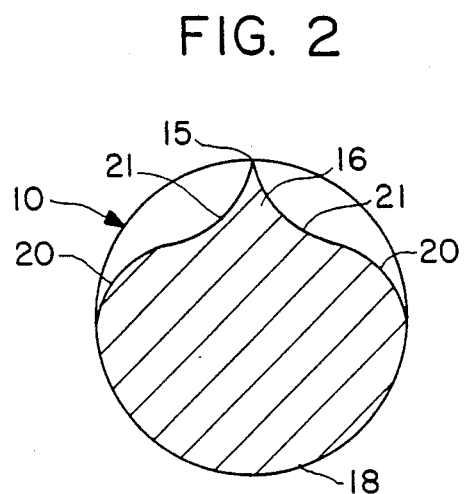
FIG. 2 is a sectional view taken along the line 2—2 of FIG. 1 of a first embodiment of the invention.

In a first embodiment illustrated in FIGS. 1 and 2, said central portion 11 has a substantially drop-shaped transverse cross-section and has a lateral surface consisting of a semicylindrical portion 18 which is a continuation of the corresponding part of portion 10, while the remainder, having the same plane of symmetry as said portion 18, has two portions 20, which are externally convex, connecting said portion 18 with the lateral surfaces 21 of cutting member 16. Said cylindrical surfaces 21, having an externally directed concavity, by means of their line of intersection give rise to edge 15 of said member 16, lying along the axis of symmetry of the said section, at a distance from the longitudinal axis of the bolt equal to the radius of said portion 18. In this way said edge 15 forms a prolongation of a generatrix of upper portion 10 and in turn extends into a generatrix of portion 12.

Figure 3:
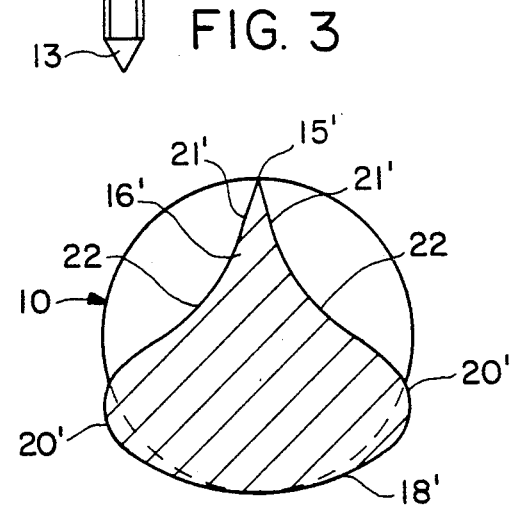
FIG. 3 is a sectional view, similar to that of FIG. 2, of a second embodiment of the invention.

A second embodiment of the invention provides a central portion 11' having a transverse cross-section which is again substantially in the form of a drop as illustrated in FIG. 3.

Said portion 11' has a symmetrical lateral surface with respect to a plane passing through the longitudinal axis of the bolt consisting of a cylindrical portion 18' with a radius of curvature slightly greater than the radius of cylindrical portion 10, having its generatrix lying in the same plane of symmetry, as an extension to the generatrix of said portion 10, while the remaining portion has two portions 20' of variable curvature, which are externally convex, followed by two other portions 22, which are internally convex, joining said portion 18' with the lateral surfaces 21' of cutting member 16'.

By their intersection said flat surfaces 21' determine the edge 15' of said member 16' lying along the axis of symmetry of the said portion, at a distance from the longitudinal axis of the bolt equal to the radius of said portion 10.

Figure 4:
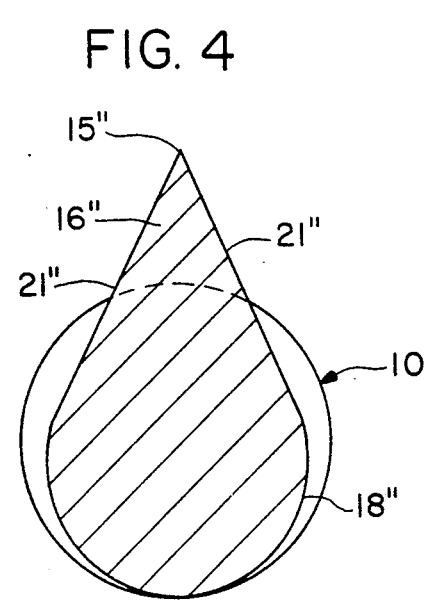
FIG. 4 is a sectional view, similar to that of FIG. 2, of a third embodiment of the invention.

FIG. 4 illustrates the transverse cross-section of central portion 11" of a third embodiment of the invention.

Central portion 11" has a transverse cross-section which is still substantially in the shape of a drop and has a lateral surface which is symmetrical with respect to a plane passing through the longitudinal axis of the bolt. The said lateral surface consists of a cylindrical portion 18" having a radius of curvature slightly less than the radius of cylindrical portion 10, the generatrix of which lies in the same plane of symmetry and is the extension of a generatrix of said portion 10, while the remaining portion consists of the two lateral surfaces 21" of cutting member 16". Through the line of their intersection said surfaces 21" give rise to the edge 15" of said member 16". Said edge 15" which lies in the plane of symmetry of the cross-section runs parallel to the longitudinal axis of the bolt at a distance from it of slightly more than the radius of cylindrical portion 10.

Clearly in order to limit the danger of cutting persons who come into accidental contact with such bolts when they are being handled said edge 15" is merged into the surfaces of portions 10 and 12 at the two ends of portion 11" so as not to leave sharp edges.

Even though not illustrated in the drawings, it is clear that portion 12 may be tapering or cylindrical, and may be provided with any known thread, either tapering or cylindrical. It is also clear that end 14 of the bolt according to the invention may also be shaped in a different manner from that illustrated provided that the said bolt can be engaged by a suitable instrument for tightening or slackening it.

Finally, it is clear that point 13 of the bolt may also not be pointed as illustrated in FIG. 1, but taper in a different way.

We claim:

1. A bolt for orthopaedic surgical use for the elongation of bones, which can be used with an external fixing device, said bolt comprising:
   (a) a substantially cylindrical upper portion having an upper end adapted to turn the bolt by means of a suitable instrument,
   (b) a lower threaded portion which terminates at its end in a point,
   (c) a central portion located between said upper and lower portions, the lateral surface of said central portion defining on one side a cutting member having a cutting edge which extends parallel to the longitudinal axis of the bolt over the entire length of the central portion, and in which the other side of the lateral surface of said central portion is graded into the lateral surfaces of the upper portion and the lower portion in order to eliminate sharp edges at the transition between the central and upper portion and the central and lower portion, said central portion remaining outside of the bone during the elongation process.

2. A bolt according to claim 1, having a central portion, said central portion having a cross-section substantially in the shape of a drop, having a bottom surface consisting of a semicylindrical portion forming an extension of the corresponding part of the upper portion and lower portion of the bolt and, a remaining portion, having the same plane of symmetry as the semicylindrical portion, has two curved portions with outwardly directed convexity joining the semicylindrical portion with two curved portions with inwardly directed concavity, the line of intersection of the two curved portions with inwardly directed concavity forming the edge of the cutting member, said edge of cutting member terminating at a point equal to the circumference of the upper portion of the bolt.

3. A bolt according to claim 1, having a central portion, said central portion having a cross-section which is substantially drop-shaped, the lateral surface consisting of a semicylindrical portion whose radius of curvature is slightly greater than the radius of curvature of the upper portion of the bolt, and two portions of variable curvature with outwardly directed convexity joining the semicylindrical portion with two portions of inwardly directed concavity, the line of intersection of the two curved portions with inwardly directed concavity forming the edge of said cutting member, said edge of the cutting member terminating at a point along the circumference of the upper portion of the bolt.

4. A bolt according to claim 1, having a central portion, said central portion having a cross-section substantially in the shape of a drop, the lateral surface consisting of a semicylindrical portion with a radius of curvature slightly less than the radius of curvature of the cylindrical upper portion of the bolt, and two flat lateral surfaces of the cutting member, joining with the semicylindrical portion, the line of their intersection give rise to the edge of said cutting member, said edge extending beyond the circumference of the upper portion of the bolt.

5. A bolt for the elongation of bones, which can be used with external fixing devices, comprising:
   an upper portion adapted to engage with a wrenching tool;
   a lower portion adapted to be fixedly attached within bone; and
   a central portion located between said upper and lower portions, said central portion having a drop-shaped cross section defining a cutting member, wherein said cutting member extends parallel to the longitudinal axis of said bolt over the entire length of said central portion.

6. A bolt according to claim 5, wherein said lower portion comprises a threaded portion which terminates at its end in a point.

7. A bolt according to claim 5, wherein said upper portion is substantially cylindrical in cross-section.

8. A bolt according to claim 5 wherein said upper portion has a first width, said lower portion has a second width, and said central portion has a third width, said third width exceeding said second width.

9. A bolt according to claim 7, wherein said drop-shaped cross-section has a bottom part consisting of a semicylindrical portion forming an extension of the corresponding part of the upper portion and lower portion of the bolt, and a remaining portion having two curved portions with outwardly directed convexity, said two curved portions being joined integrally to opposite sides of the semicylindrical portion, and two curved portions with inwardly directed concavity, one each integrally joining said two curved portions with outwardly directed, the line of intersection of the two curved portions with inwardly directed concavity forming the point of the drop-shaped cross-section and the edge of the cutting member, said edge of the cutting member terminating at a point equal to the circumference of the upper portion of the bolt.

10. A bolt according to claim 7, wherein said drop-shaped cross-section has a bottom part consisting of a semicylindrical portion whose radius of curvature is slightly greater than the radius of curvature of the upper portion of the bolt, and a remaining portion having two curved portions with outwardly directed convexity, said two curved portions being joined integrally to opposite sides of the semicylindrical portion and two portions of inwardly directed concavity, one each integrally joining said two curved portions with outwardly directed convexity, the line of intersection of the two curved portions with inwardly directed concavity forming the point of the drop-shaped cross-section and the edge of said cutting member, said edge of the cutting member terminating at a point along the circumference of the upper portion of the bolt.

11. A bolt according to claim 7, wherein said drop-shaped cross-section has a bottom part consisting of a semicylindrical portion whose radius of curvature is slightly less than the radius of curvature of the upper portion of the bolt, and a remaining portion having two flat lateral portions, said two flat lateral portions being joined integrally to opposite sides of the semicylindrical portion, the line of the intersection of said two flat lateral portions forming the point of the drop-shaped cross-section and the edge of said cutting member, said edge extending beyond the circumference of the upper portion of the bolt.

* * * * *